United States Patent

Reiffenrath et al.

Patent Number: 5,122,297
Date of Patent: Jun. 16, 1992

[54] TETRACYCLIC BENZENE DERIVATIVES AND LIQUID-CRYSTALLINE MEDIA

[75] Inventors: Volker Reiffenrath, Rossdorf; Reinhard Hittich, Modautal; Herbert Plach, Darmstadt, all of Fed. Rep. of Germany

[73] Assignee: Merck Patent Gesellschaft MIT Beschrankter Haftung, Darmstadt, Fed. Rep. of Germany

[21] Appl. No.: 691,275

[22] Filed: Apr. 25, 1991

[30] Foreign Application Priority Data

Apr. 26, 1990 [DE] Fed. Rep. of Germany ....... 4013241

[51] Int. Cl.⁵ .............. C09K 19/30; C09K 19/12; C09K 19/52; C07C 41/00; C07C 15/12
[52] U.S. Cl. .................. 252/299.63; 252/299.01; 252/299.6; 252/299.66; 568/631; 568/642; 568/645; 568/656; 370/129; 370/182
[58] Field of Search ........... 252/299.1, 299.6, 299.63, 252/299.66, 299.5; 568/621, 642, 645, 656; 570/129, 182; 585/25

[56] References Cited

U.S. PATENT DOCUMENTS

| | | | |
|---|---|---|---|
| 4,545,922 | 10/1985 | Eidenschink et al. | 252/299.63 |
| 4,620,938 | 11/1986 | Römer et al. | 252/299.63 |
| 4,797,228 | 1/1989 | Goto et al. | 252/299.63 |
| 5,032,313 | 7/1991 | Goto | 252/299.63 |
| 5,061,400 | 10/1991 | Obikawe | 252/299.63 |

Primary Examiner—John S. Maples
Assistant Examiner—Shean C. Wu
Attorney, Agent, or Firm—Millen, White & Zelano

[57] ABSTRACT

The invention relates to novel tetracyclic benzene derivatives of the formula I in which n is 1 to 7, A is trans-1,4-cyclohexylene, 1,4-phenylene, 3-fluoro-1,4-phenylene or 3,5-difluoro-1,4-phenylene, X is F, Cl, CF₃, —OCF₃ or —OCHF₂, and L, Y and Z are each, independently of one another, H or F.

7 Claims, No Drawings

TETRACYCLIC BENZENE DERIVATIVES AND LIQUID-CRYSTALLINE MEDIA

BACKGROUND OF THE INVENTION

The invention relates to tetracyclic benzene derivatives of the formula I

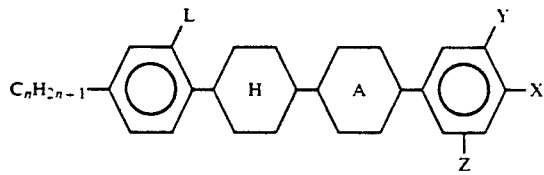

in which n is 1 to 7, A is trans-1,4-cyclohexylene, 1,4-phenylene, 3-fluoro-1,4-phenylene or 3,5-difluoro-1,4-phenylene, X is F, Cl, CF$_3$, —OCF$_3$ or —OCHF$_2$, and L, Y and Z are each, independently of one another, H or F.

DE-A 3 734 116 discloses liquid crystals of the formula B

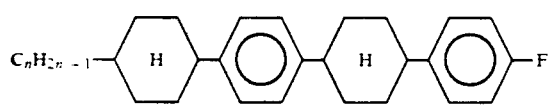

The compounds B are distinguished only by moderate dielectric anisotropy, which frequently results in relatively high threshold voltages in mixtures.

Like similar compounds, for example, those known from DE-A 32 11 601, the compounds of the formula I can be used as components of liquid-crystalline media, in particular for displays based on the principle of the twisted cell. See, also, copending application Ser. No. 07/623,385, filed Nov. 19, 1990, claiming priority to DE 39 29 525.7 and DE 39 29 526.5, both filed Sep. 6, 1989, DE 39 29 764.0, filed Sep. 7, 1989, and DE 40 09 907.5, filed Mar. 23, 1990; copending application Ser. No. 07/677,891 filed Apr. 1, 1991, and claiming priority to DE 40 10 447.8, filed Mar. 31, 1990; and PCT International Application No. PCT/EP90/01649, claiming priority of GB 89 22 168.3, filed Oct. 2, 1989, and other foreign applications filed after that date.

The substances employed hitherto for this purpose all have certain disadvantages, for example, excessively high melting points, excessively low clearing points, inadequate stability toward the action of heat, light or electrical fields, inadequate electrical resistance, and excessive temperature dependence of the threshold voltage.

The materials employed hitherto have disadvantages, in particular in displays of the super twist type (STN) having twist angles of significantly greater than 220° or in displays having an active matrix.

SUMMARY OF THE INVENTION

This invention provides novel liquid-crystalline compounds which are suitable as components of liquid-crystalline media, in particular, for nematic media having positive dielectric anisotropy, and which do not have the disadvantages of the known compounds, or only do so to a lesser extent. These novel compounds are of the formula I above.

This invention also provides liquid-crystalline media which contain the compounds of formula I, methods for their production, and electrooptical displays which contain these liquid-crystalline media.

It has been found that the compounds of the formula I are eminently suitable as components of liquid-crystalline media. In particular, they can be used to prepare liquid-crystalline media having broad nematic ranges, high clearing points, excellent nematogeneity down to low temperatures, excellent chemical stability, pronounced $\epsilon\perp$ at positive dielectric anisotropy, low temperature dependence of the threshold voltage and/or low optical anisotropy. In addition, the novel compounds have good solubility for other components of media of this type and high positive dielectric anisotropy at the same time as favorable viscosity.

The compounds of the formula I facilitate both STN displays having a very steep electrooptical characteristic line and displays having an active matrix and excellent long-term stability.

In the pure state, the compounds of the formula I are colorless and form liquid-crystalline mesophases in a temperature range which is favorably located for electrooptical use.

The invention thus relates to compounds of the formula I and to the use of the compounds of the formula I as components of liquid-crystalline media, to liquid-crystalline media containing at least one compound of the formula I, and to electrooptical displays which contain media of this type.

Below, n, A, L, X, Y and Z are as defined above, unless expressly stated otherwise.

In the compounds of the formula I, the alkyl groups C$_n$H$_{2n-1}$ are preferably straight-chain. Accordingly, C$_n$H$_{2n-1}$ is methyl, ethyl, n-propyl, n-butyl, n-pentyl, n-hexyl or n-heptyl. n is preferably 2, 3, 4 or 5.

Compounds of the formula I having branched alkyl groups may occasionally be of importance due to better solubility in the customary liquid-crystalline base materials, but in particular as chiral dopes if they are optically active. Branched groups of this type generally contain not more than one chain branch. Preferred branched alkyl radicals are isopropyl, 2-butyl, (=1-methylpropyl), isobutyl (=2-methylpropyl), 2-methylbutyl, isopentyl (=3-methylbutyl), 2-methylpentyl, 3-methylpentyl and 2-heptyl (=1-methylhexyl). The radical

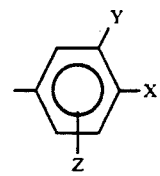

is preferably

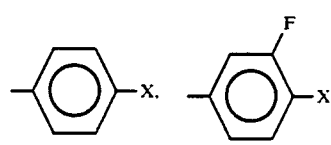

or

-continued

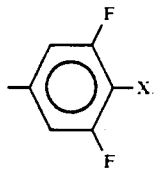

X is preferably F, Cl, —CF₃ or —OCF₃.

Particularly preferred compounds are those of the sub-formulae below:

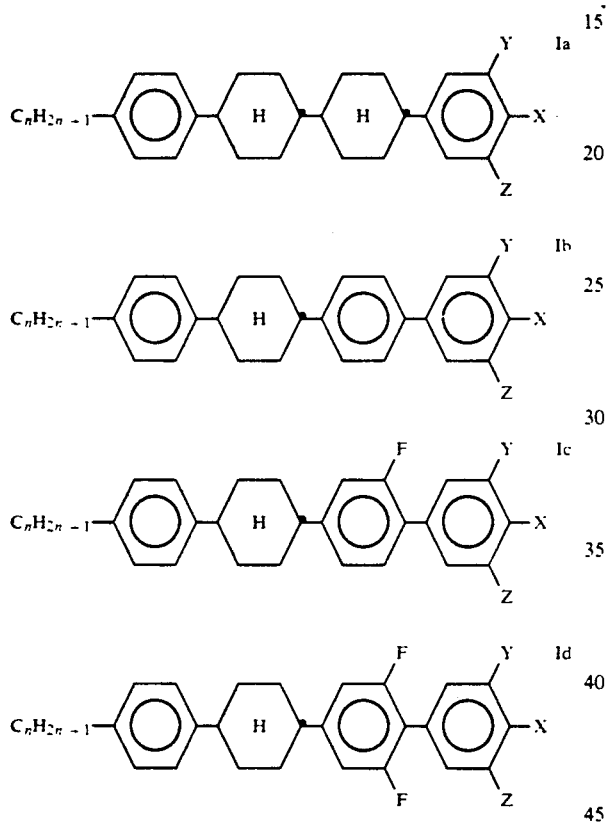

in which n, X, Y and Z are as defined above.

In addition, the compounds of the formula I are prepared by methods which are known per se, as described in the literature (for example in the standard works such as Houben-Weyl, Methoden der Organischen Chemie [Methods of Organic Chemistry] Georg-Thieme-Verlag, Stuttgart), to be precise under reaction conditions which are known and are suitable for the reactions mentioned. Use may also be made here of variants which are known per se, but are not described here in greater detail.

If desired, the starting materials can also be formed in situ by not isolating them from the reaction mixture, but instead immediately reacting them further to form the compounds of the formula I.

The compounds of the formula I can be prepared, for example, in accordance with the following synthesis schemes:

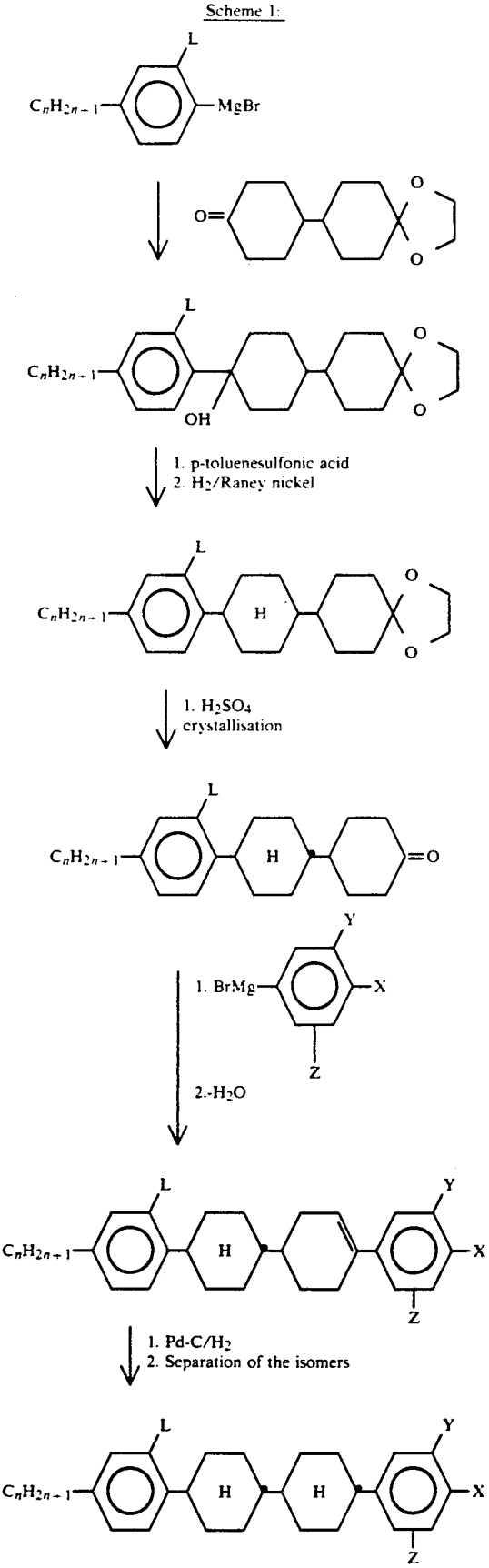

Scheme 2

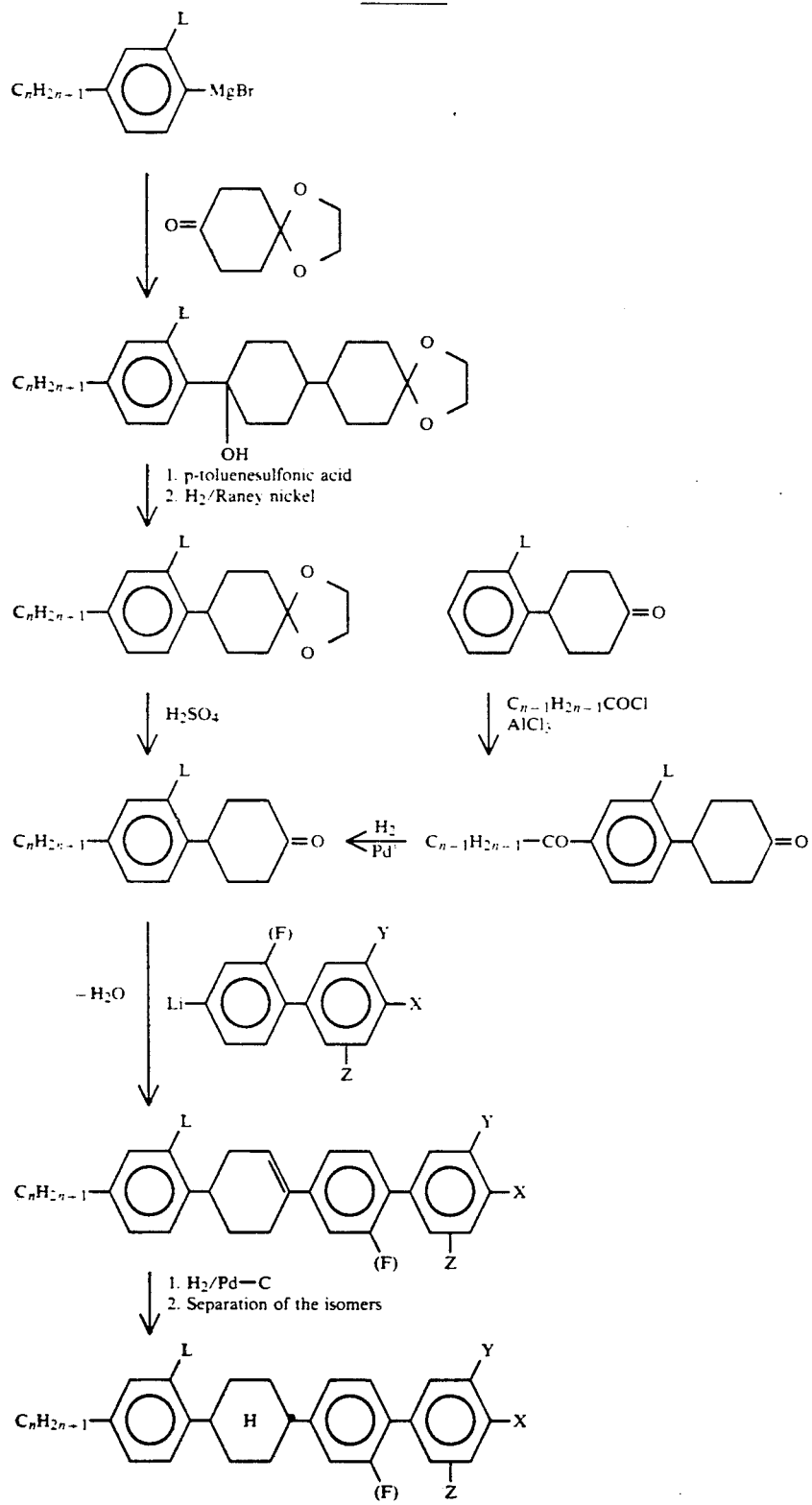

Some of the bromobiphenyl derivatives used as starting materials are known, and some can be prepared without difficulties to form compounds known from the literature by standard methods of organic chemistry. For example, the $OCF_3$ or $OCHF_2$ compounds can be obtained by known methods from the corresponding phenols and the $CF_3$ or CN compounds from the corresponding benzoic acids. Compounds of the formula

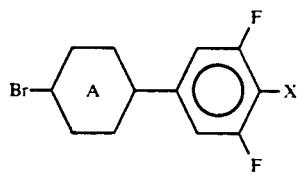

and the corresponding monofluorinated compounds can be obtained, for example, from the known precursors where X=H by lithiation at low temperatures, and subsequent reaction with a suitable electrophile.

Further variants of the synthesis are known to those skilled in the art. All the starting materials are either known or can be prepared analogously to known compounds.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylicacid,phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbgenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenyl-cyclohexyl)ethanes, 1-cyclohexyl-2-biphenylylethanes, 1-phenyl-2-cyclohexylphenylethanes and tolans.

The 1,4-phenylene groups in these compounds may also be fluorinated.

The most important compounds suitable as further constituents of media according to the invention can be characterized by the formulae 1, 2, 3, 4 and 5:

R'-L-E-R"  1

R'-L-COO-E-R"  2

R'-L-OOC-E-R"  3

R'-L-CH$_2$CH$_2$-E-R"  4

R'-L-C≡C-E-R"  5

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, —OCF$_3$, F, Cl or —NCS; in this case, R has the meaning given for the compounds of the sub-formulae 1a to 5a and is preferably alkyl or alkenyl. R" is preferably selected from the group comprising —F, Cl, CF$_3$ and —OCF$_3$. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed.

Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 40 13 241.2, are hereby incorporated by reference.

The examples below are intended to illustrate the invention without representing a limitation. mp.=melting point, cp.=clear point. Above and below, percentages are per cent by weight; all temperatures are indicated in degrees Celsius. "Customary work-up" means that water is added, the mixture is extracted with methylene chloride, and the organic phase is separated off, dried and evaporated, and the product is purified by crystallization and/or chromatography.

In addition, the abbreviations have the following meanings:

C: crystalline-solid state, S: smectic phase (the index characterises the phase type), N: nematic state,
Ch: cholesteric phase, I: isotropic phase. The number between two symbols indicates the conversion temperature in degrees Celsius.
DAST: diethylaminosulfur trifluoride
DCC: Dicyclohexylcarbodiimide
DDQ: dichlorodicyanobenzoquinone
DIBALH: diisobutylaluminium hydride
DMSO: dimethyl sulfoxide
POT: potassium tertiary-butanolate
THF: tetrahydrofuran
pTSOH: p-toluenesulfonic acid

EXAMPLES

Example 1

1-(3,4-difluorophenyl)-4-[trans-4-(p-propylphenyl)-cyclohexyl]-cyclohexene, which obtained in accordance with Scheme I, is hydrogenated in a manner known per se on Pd/C at room temperature. Customary work-up by chromatography and crystallisation gives trans-1-(3,4-difluorophenyl)-4-[trans-4-(p-n-propylphenyl)-cyclohexyl]-cyclohexane.

Examples 2 to 64

The following compounds are obtained analogously to Example 1:

| | n | X | Y | Z | L | A |
|---|---|---|---|---|---|---|
| (7) | 3 | F | F | F* | H | Ph |
| (8) | 5 | Cl | F | F* | H | Ph |
| (9) | 2 | Cl | F | F* | H | Ph |
| (10) | 3 | Cl | F | F* | H | Ph |
| (11) | 5 | -OCF$_3$ | H | H | H | Ph |
| (12) | 2 | -OCF$_3$ | H | H | H | Ph |
| (13) | 3 | -OCF$_3$ | H | H | H | Ph |
| (14) | 5 | -OCHF$_2$ | H | H | H | Ph |
| (15) | 2 | -OCHF$_2$ | H | H | H | Ph |
| (16) | 3 | -OCHF$_2$ | H | H | H | Ph |
| (17) | 2 | F | H | H | H | Cy |
| (18) | 3 | F | H | H | H | Cy |
| (19) | 5 | F | H | H | H | Cy |
| (20) | 2 | Cl | H | H | H | Cy |
| (21) | 3 | Cl | H | H | H | Cy |
| (22) | 5 | Cl | H | H | H | Cy |
| (23) | 2 | F | F | H | H | Cy |
| (24) | 4 | F | F | H | H | Cy |
| (25) | 5 | F | F | H | H | Cy |
| (26) | 2 | Cl | F | H | H | Cy |
| (27) | 3 | Cl | F | H | H | Cy |
| (28) | 5 | Cl | F | H | H | Cy |
| (29) | 2 | -CF$_3$ | H | H | H | Cy |
| (30) | 3 | -CF$_3$ | H | H | H | Cy |
| (31) | 5 | -CF$_3$ | H | H | H | Cy |
| (32) | 3 | -CF$_3$ | F | H | H | Cy |
| (33) | 3 | -CF$_3$ | F | H | H | Cy |
| (34) | 5 | -CF$_3$ | F | H | H | Cy |
| (35) | 2 | F | H | H | F | Cy |
| (36) | 3 | F | H | H | F | Cy |
| (37) | 5 | F | H | H | F | Cy |
| (38) | 2 | F | F | H | F | Cy |
| (39) | 3 | F | F | H | F | Cy |
| (40) | 5 | F | F | H | F | Cy |
| (41) | 2 | F | F | F* | H | Cy |
| (42) | 3 | F | F | F* | H | Cy |
| (43) | 5 | F | F | F* | H | Cy |
| (44) | 2 | -OCF$_3$ | H | H | H | Cy |
| (45) | 3 | -OCF$_3$ | H | H | H | Cy |
| (46) | 5 | -OCF$_3$ | H | H | H | Cy |
| (47) | 2 | -OCHF$_2$ | H | H | H | Cy |
| (48) | 3 | -OCHF$_2$ | H | H | H | Cy |
| (49) | 5 | -OCHF$_2$ | H | H | H | Cy |
| (50) | 2 | F | F | H | H | PhF |
| (51) | 3 | F | F | H | H | PhF |
| (52) | 5 | F | F | H | H | PhF |
| (53) | 2 | Cl | F | H | H | PhF |
| (54) | 3 | Cl | F | H | H | PhF |
| (55) | 5 | Cl | F | H | H | PhF |
| (56) | 2 | F | H | H | H | PhF |
| (57) | 3 | F | H | H | H | PhF |
| (58) | 5 | F | H | H | H | PhF |
| (59) | 2 | -CF$_3$ | H | H | H | PhF |
| (60) | 3 | -CF$_3$ | H | H | H | PhF |
| (61) | 5 | -CF$_3$ | H | H | H | PhF |
| (62) | 2 | -OCF$_3$ | H | H | H | PhF |
| (63) | 3 | -OCF$_3$ | H | H | H | PhF |
| (64) | 5 | -OCF$_3$ | H | H | H | PhF |

*Z in the ortho-position to X (Ph = 1,4-phenylene, Cy = trans-1,4-cyclohexylene, PhF = 3-fluoro-1,4-phenylene)

Example 65

Synthesis of

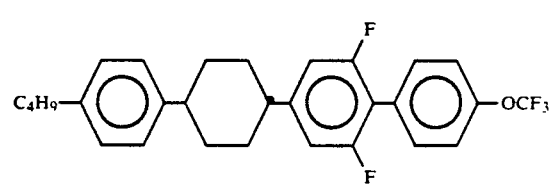

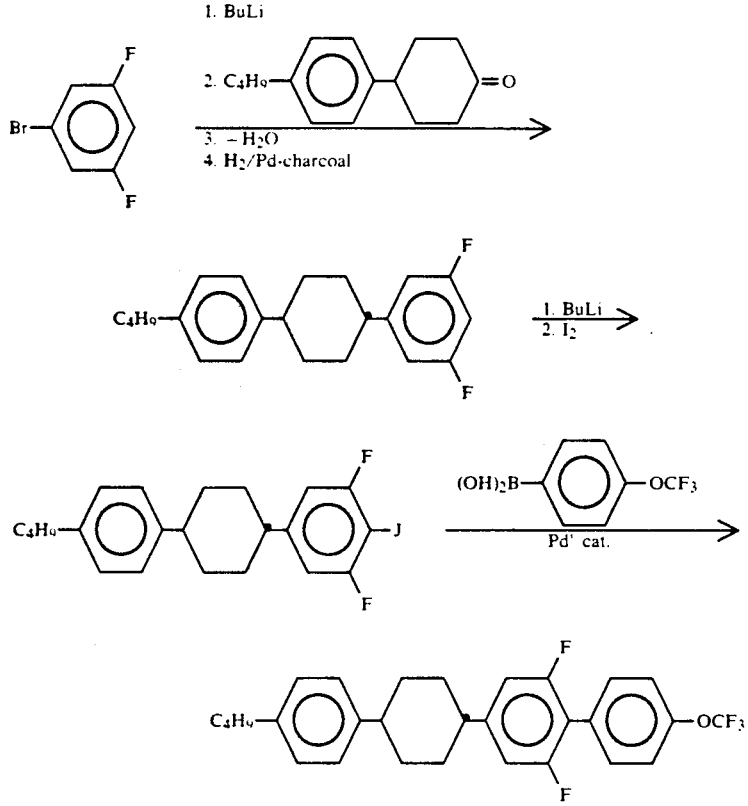

0.1 m of the difluoroiodobenzene derivative and 0.1 m of 4-trifluoromethoxyphenylboric acid are dissolved in a mixture of 210 ml of toluene and 85 ml of ethanol, and after 2.6 g of tetrakis(triphenylphosphine)palladium-O and 105 ml of saturated $Na_2CO_3$ solution are added, the mixture is refluxed for four hours with stirring. Extractive work-up followed by chromatography and crystallisation gives the product.

The following compounds where

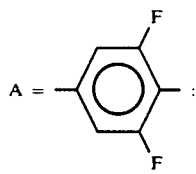

are obtained analogously to Example 65:

| | n | X | Y | Z | L |
|---|---|---|---|---|---|
| (66) | 2 | F | F | H | H |
| (67) | 3 | F | F | H | H |
| (68) | 5 | F | F | H | H |
| (69) | 2 | Cl | F | H | H |
| (70) | 3 | Cl | F | H | H |
| (71) | 5 | Cl | F | H | H |
| (72) | 2 | F | H | H | H |
| (73) | 4 | F | H | H | H |
| (74) | 5 | F | H | H | H |
| (75) | 2 | -CF$_3$ | H | H | H |
| (76) | 3 | -CF$_3$ | H | H | H |
| (77) | 5 | -CF$_3$ | H | H | H |
| (78) | 2 | -OCF$_3$ | H | H | H |
| (79) | 3 | -OCF$_3$ | H | H | H |
| (80) | 5 | -OCF$_3$ | H | H | H |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula I

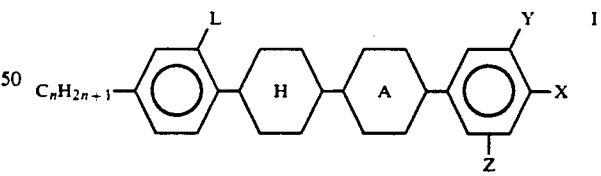

wherein n is 1 to 7, A is 3-fluoro-1,4-phenylene or 3,5-difluoro-1,4-phenylene, X is F, Cl, CF$_3$, —OCF$_3$ or —OCHF$_2$, and L, Y and Z are each, independently of one another, H or F.

2. A compound of claim 1, having the formula Ic

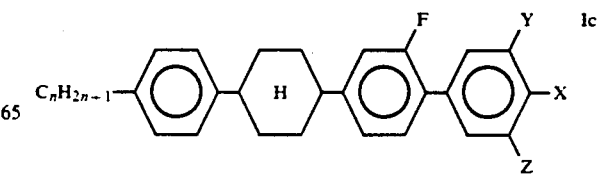

in which n, X, Y and Z are as defined in claim 1.

3. A compound of claim 1, having the formula Id

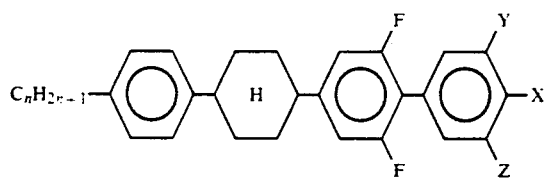

in which n, X, Y and Z are as defined in claim 1.

4. A method of producing liquid-crystalline media for electrooptical displays, the improvement comprising adding as one or more components of the liquid-crystalline media a compound of claim 1.

5. A liquid-crystalline medium containing at least two liquid-crystalline components, wherein at least one component is a compound of claim 1.

6. An electrooptical display based on a liquid-crystal cell which contains a liquid-crystalline medium of claim 7.

7. A compound of claim 1, wherein n is 2, 3, 4 or 5.

* * * * *